United States Patent [19]

Langen et al.

[11] Patent Number: 4,984,570

[45] Date of Patent: Jan. 15, 1991

[54] KNITTED HYDROPHOBIC WEB WOUND DRESSING

[75] Inventors: Günter Langen, Wolfstein; Harald Jung, Kreimbach-Kaulb, both of Fed. Rep. of Germany

[73] Assignee: Karl Otto Braun KG, Wolfstein, Fed. Rep. of Germany

[21] Appl. No.: 408,411

[22] Filed: Sep. 14, 1989

Related U.S. Application Data

[63] Continuation of Ser. No. 41,678, Apr. 21, 1987, abandoned.

[30] Foreign Application Priority Data

Apr. 22, 1986 [EP] European Pat. Off. ........ 86105530.9

[51] Int. Cl.$^5$ ..................... A61L 15/00; A61F 13/00; A61F 15/00
[52] U.S. Cl. ................................. 128/156; 128/155; 604/304
[58] Field of Search ............... 128/155, 156, 157, 165, 128/169; 604/304, 384, 385 R; 66/169 R, 170, 193, 201, 202; 2/DIG. 1; 424/447

[56] References Cited

U.S. PATENT DOCUMENTS

| | | | |
|---|---|---|---|
| 2,230,067 | 1/1941 | Pedlow ................................. | 66/170 |
| 2,711,168 | 6/1955 | Brickman et al. ................... | 128/156 |
| 2,899,812 | 8/1959 | Attenborough ...................... | 66/169 |
| 3,249,109 | 5/1966 | Maeth et al. ......................... | 604/304 |
| 3,367,333 | 2/1968 | Scheier ................................. | 604/384 |
| 3,421,502 | 1/1969 | St. Clair .............................. | 128/156 |
| 3,682,179 | 8/1972 | Firth et al. .......................... | 128/157 |
| 4,323,061 | 4/1982 | Usukura .............................. | 128/156 |
| 4,542,739 | 9/1985 | Schafer ............................... | 128/156 |

FOREIGN PATENT DOCUMENTS

| | | |
|---|---|---|
| 0099758 | 2/1984 | European Pat. Off. . |
| 0652379 | 10/1937 | Fed. Rep. of Germany ...... 128/156 |
| 2460029 | 6/1976 | Fed. Rep. of Germany ...... 424/447 |
| 1296044 | 5/1962 | France .................... 66/170 |
| 2119721 | 8/1972 | France . |
| 2281099 | 3/1976 | France . |
| 2525245 | 10/1983 | France . |
| 0562909 | 1/1981 | Japan .................... 604/897 |

*Primary Examiner*—Randall L. Green
*Assistant Examiner*—Paul Prebilic
*Attorney, Agent, or Firm*—Toren, McGeady & Associates

[57] ABSTRACT

The textile fabric is used as a wound dressing in much the same way as dressing gauze with improved characteristics compared with the latter and comprises a central web portion of man-made fibers having a high surface tension, and on either side thereof web portions formed from absorbent, cellulosic yarns. The central web portion is connected by looping to the outer web portions so that after folding, a nonstick wound dressing is obtained in which the hydrophobic man-made fibers functioning as the wound covering, come to rest on the wound, while the folded layers of cellulosic fibers behind it, act as an absorbent layer.

11 Claims, 2 Drawing Sheets

KNITTED HYDROPHOBIC WEB WOUND DRESSING

This is a continuation of Ser. No. 07/041,678, filed Apr. 21, 1987, abandoned.

BACKGROUND OF THE INVENTION

The invention relates to a textile fabric for wound care.

For the textile covering of wounds, it is conventional practice to use textile fabrics based on woven, knitted or non-woven fabrics, as well as combinations thereof.

A wound dressing must protect the wound from infection and aid healing and an ideal dressing or bandage material has the following characteristics:

(a) high absorptivity and porosity, because liquid accumulations provide ideal conditions for colonization by germs and for infection of a wound, (b) must not cause heat accumulation, i.e. the temperature in the vicinity of the wound must not be increased due to the dressing, (c) is subject to minimum tensile strength, particularly wet tensile strength, (d) must be easily applicable and sterilizable by known methods, (e) must conform readily and easily to the wound without folds or creases, and not have any shrinking tendency, (f) must be physiologically impeccable, i.e. non-irritating, (g) must be permeable to air and in particular the pore size of the textile fabric must be in a given relation to the thread thickness. If the pore size is too small, accumulation of secretion, sticking of the wound and air exclusion will occur.

For wound covering purposes, it is known to use gauze dressings of wide-meshed fabric made of cotton, viscose or a combination thereof and for covering the wound, the gauze is folded in multilayer compresses of different size and thickness. Gauze dressings made from pure cotton have proved satisfactory as a wound care material for many decades and are still the most commonly used dressing material due to their high economy and due to the reasons given hereinafter:

(1) high absorptivity, high liquid retention capacity,
(2) high stability in dry and wet state,
(3) high bulk elasticity, good cushioning effect,
(4) high permeability to air and water vapour,
(5) good plastic conforming capacity,
(6) versatile use and at the same time very inexpensive,
(7) chemical purity.

However, the wound covering using pure gauze dressings does not satisfy all properties required of such a dressing. In the case of sticking and encrustation, accumulations of secretion can occur and when removing such a stuck dressing, the fresh granulations and epithelial edges are torn open so that once again bleeding, injury and pain occur. When changing a dressing which is sticking to the wound, the wound is torn open again and thereby the healing process is disturbed and interrupted. Gauze dressings are generally available in bulk form of 40 meters length and in various widths and are mainly used for transformation into compresses, swabs, stomach coverings, etc. A prefabricated form is zig-zag gauze or conditioned and/or mechanically compressed, folded material on rolls in socalled dispensers.

In conventional gauze compresses which are e.g. 4-ply, 6-ply, 8-ply, 12-ply and 16-ply, the cut edges are folded into the body of the compress so that during the folding procedure fibre residues are prevented from escaping and getting into the wound.

Apart from gauze dressings, wound-friendly dressings are known, such as those with a movement effect. By using varingly twisted and thick threads, a textile fabric is produced by weaving or knitting from pure viscose which reacts to water and liquid secretion by bending and moving. Due to this movement effect, under the action of liquid the fabric is raised from the wound in tunnel-like manner and prevents sticking. Thus, sticking of the textile threads to the wound is prevented by lift-off action, i.e. purely mechanically.

DE-A-22 61 889 discloses a compress, particularly for medical, surgical and other uses, in which a mesh strip is used as a basis, being produced in such a way on a mesh loom that said strip provides edges and an air-permeable, open texture with small, lengthwise extending warp threads which are interconnected by cross threads, the strip or the superimposed strips with edges being cut to the appropriate length and folded back in such a way that a compress in the required measurements is being formed. Such a compress is intended to eliminate any risk of separating into fibres. This compress is a gauze-like knitted fabric, in which the escape of fibre fragments is to be prevented by so-called blocked meshes. The technical physical and chemical characteristics are largely identical with those of gauze dressings.

DE-A-14 92 434 discloses a wound dressing material comprising a knitted textile fabric, in which a thick thread is linked by a looped thin thread, in which the thick thread is highly twisted, straight or in slightly displaced stationary weft and is linked by at least one thread with minimum twist. Due to the fact that this wound dressing material has different yarn dimensions and twists, the thread shortens when wetted so that the dressing material is raised off the wound surface. This leads to a non-stick effect. As a result of the relatively dense thread structure, said wound dressing material can only be used to a limited extent as a compress, due to lack of plasticity.

DE-A-32 13 673 describes a wound dressing material, particularly for adhesive first aid dressings with the special aim of permitting the gentle changing of the dressing. This constitutes an atraumatic wound dressing material. The special feature achieved by said material results from a combination between hydrophobic polyester fibres on the wound side and highly absorbent rayon staple yarns in a textile compound structure.

Another group of textile wound dressings is constituted by non-woven fabrics, in the form of a fibre compound, the individual fibres being mechanically, thermally or chemically interconnected. In most cases viscose fibres are used for such textile fabrics. The strength of such textile fabrics is extremely low due to the fibre compound and material used. In particular, the wet tensile strength is well below that of woven and knitted fabrics. The bulk elasticity is also low. The problem of protruding fibres can only be solved by an additional treatment with synthetic resin dispersions or by laminating of perforated films.

In addition, a number of combined wound dressing materials based on gauze dressings are known, such as e.g. cotton wool/gauze or cellulose/gauze compresses. The water holding capacity of such compresses is increased by the cellulose or cotton wool part serving as the inner absorbent body, but the gauze layer is in contact with the wound and it is not possible to prevent sticking between gauze layer and wound.

The present invention is solving the problem to provide an open-pore, air-permeable, knitted textile fabric not sticking to the wound with dressing gauze-like, but improved characteristics, which ensures maximum wound rest and which when folded represents a wound compress with a hydrophobic covering layer which is in contact with the wound and with hydrophilic absorbent layers located above the same and which in addition has a higher minimum tensile strength compared to dressing gauze.

SUMMARY OF THE INVENTION

According to the invention this problem is solved by a textile fabric for wound care, wherein in a wide-knitted or raschel-knitted web of absorbent, hydrophilic, cellulose fibre yarns, such as cotton, viscose, cotton/-viscose staple, etc., is incorporated at least one strip-like web portion of hydrophobic man-made fibre yarns of synthetic polymers with a high surface tension, such as e.g. from polyamide, polyester, polyethylene, polypropylene, polyacrylonitrile, polytetrafluorethylene, etc. by looping in one plane, the strip-like web portion being constructed as a central strip or edge strip in the web of the textile fabric, which can be folded to a compress in such a way that the web portion of hydrophobic man-made fibres as the hydrophobic covering layer constitutes the wound dressings and the layers of cellulose fibre yarns behind the web portion form the absorbent layer or layers.

Such a textile fabric is a wound dressing material similar to the known dressing gauze according to DIN 61630, but provides the further additional advantage compared therewith of not sticking to the wound. The textile fabric for wound dressing purpose, compared to the known dressing gauze, is characterized in that a strip-like web portion of man-made fibre yarns, comprising synthetic polymers with a high surface tension is incorporated into an open width knitted or rascheled web of absorbent, cellulose fibre yarns, such as cotton or viscose or cotton/viscose. The man-made fibre yarns used are preferably multifilament, but it is also possible to use monofilaments, as well as staple fibre yarns. The strip-like portion can e.g. be constructed as the central strip or as an edge strip of the open width knitted web and in accordance with known compresses, the knitted fabric is folded in such a way that the hydrophobic man-made fibre part is put onto the wound. The layers of cellulose fibres behind it act as the absorbent layer. The mesh size is such that no intergrowth with the fibrin structure forming during the first phase of wound healing will occur, whilst there can still be an unhindered secretion outflow through the hydrophobic layer into the hydrophilic absorbent layer in accordance with the known wick effect.

It is also possible to apply the non-sticking wound covering layer to both sides, in that through respective folding or incorporation of a second hydrophobic strip into the compress, the absorbent layer is placed completely in the interior of said compress.

As a result of this structure of a textile fabric, the hydrophobic non-sticking wound covering layer is firmly connected to the absorbent layer in such a way that there is no possibility of separation, such as e.g. in the case of film-coated non-woven fabrics.

It has surprisingly been found that through the man-made fibre proportion, the wound compress formed from the textile fabric has a much higher minimum tensile strength than required for dressing gauze, as is apparent from the following table, which is showing at the same time that important properties like the water absorption capacity, the sink time and the air permeability are not impaired:

TABLE 1

Comparative survey of the mechanical-technological data of different wound compresses

| | Gauze compress according to DIN 61630, 17 thread, 8 ex | Non-woven fabric compress | 6 layer inventive compress |
|---|---|---|---|
| Water absorption capacity according to DIN 53 923 (g/m²) | 1084 | 1057 | 1100 |
| Absorptivity, sink time (sec.) | 1 | 2 | 1 |
| Tensile strength according to DIN 53 857 (N/cm) | >80 | 33 | >160 |
| Air permeability according to DIN 53 887 (l/m² sec.) | 3500 | 1500 | 3500 |

As hydrophobic, synthetic polymers have a very low water absorptivity and virtually no swelling tendency, the optimum wound rest necessary for the healing process is in no way disturbed. It is also possible to firmly incorporate into the textile fabric X-ray contrast threads, e.g. barium sulphate-containing viscose rayon threads or synthetic polymer threads conventionally used with gauze compresses so that said contrast thread cannot detach itself.

To facilitate for both doctor and patient the positioning of a compress with one non-stick surface, the hydrophobic part of the compress can be wholly or partly marked with an indifferent dye-stuff. In the same way, the absorbent layer can be dyed or impregnated with pharmaceutically active agents, such as e.g. antibacterial substances.

Further advantageous developments of the invention can be gathered from the subclaims.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
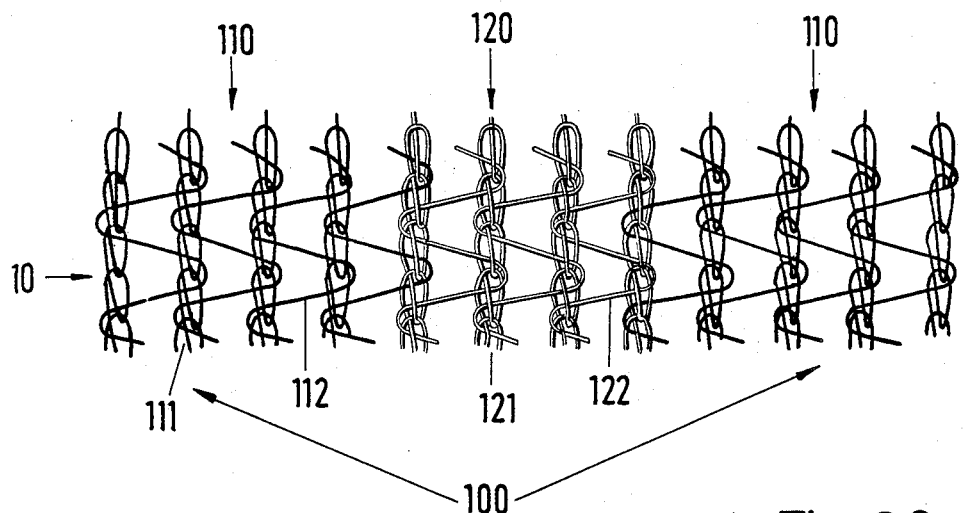
FIG. 1 A plan view of a textile fabric with a central strip forming the non-stick wound covering layer and on the other side thereof absorbent layers.
Figure 2A:
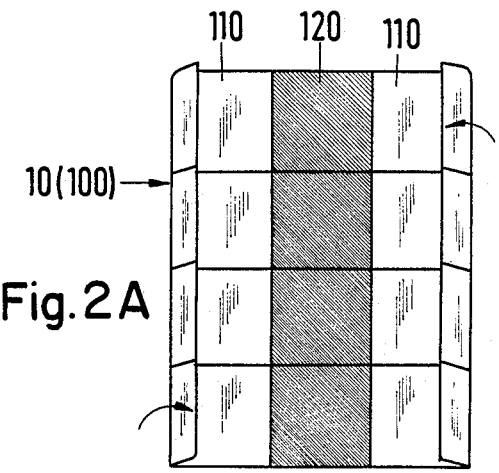
FIG. 2 Different possibilities for folding procedures of the textile fabric to form a wound compress.
Figure 2B:
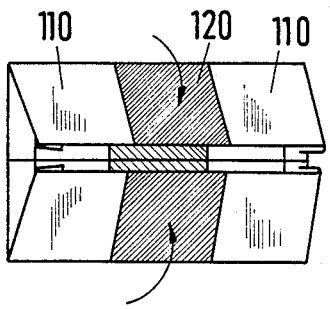
Figure 2C:
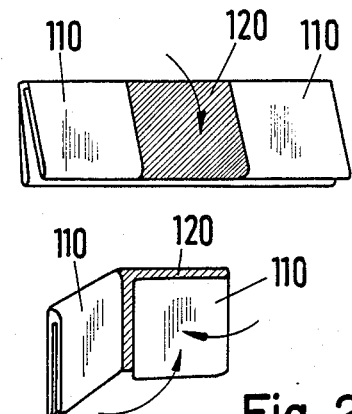
Figure 2D:
Figure 2E:
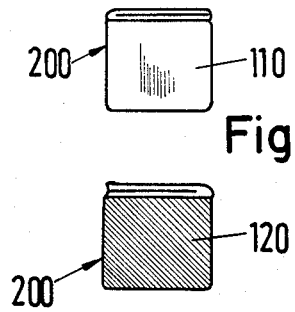
Figure 2F:
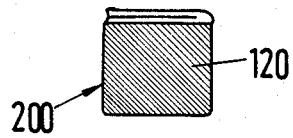

The portion of an open width knitted web 100 in FIG. 1 comprises an open width knitted or raschel-knitted textile fabric made of absorbent, i.e. hydrophilic, cellulosic fibre yarns 111, 112. At least one strip-like web portion is incorporated by looping in one plane as a central strip 120 of hydrophobic man-made fibre yarns of synthetic polymers with a high surface tension. Polyamide, polyester, polyethylene, polypropylene, polyacrylonitrile, polytetrafluoroethylene, etc. can be used as synthetic polymers. The strip-like web portion can be constructed both as a central strip or as an edge strip in the open width knitted web 100 of textile fabric 10. According to FIG. 1 web 100 comprises a central strip 120 of hydrophobic threads and to the left and right absorbent layers 110 of hydrophilic, cellulosic threads. At 111 is shown a fringe-linked stitch wale of cellulosic threads. The corresponding weft formation from cellulosic threads is indicated at 112. Stitch wale 121 is e.g. in fringe linkage from hydrophobic man-made fibre yarns, as is the weft formation 122 in said area.

FIG. 2 e.g. shows a possible folding sequence A, B, C, D, E, F of an open-width knitted web of the textile fabric with a hydrophobic wound covering layer in the form of central strip 120 and which is indicated by the hatched area. F is the wound-facing side of the folded wound compress 200 made of hydrophobic man-made fibre yarns. E is the absorbent layer remote from the wound and formed by hydrophilic, absorbent, cellulosic threads.

Figure 3:
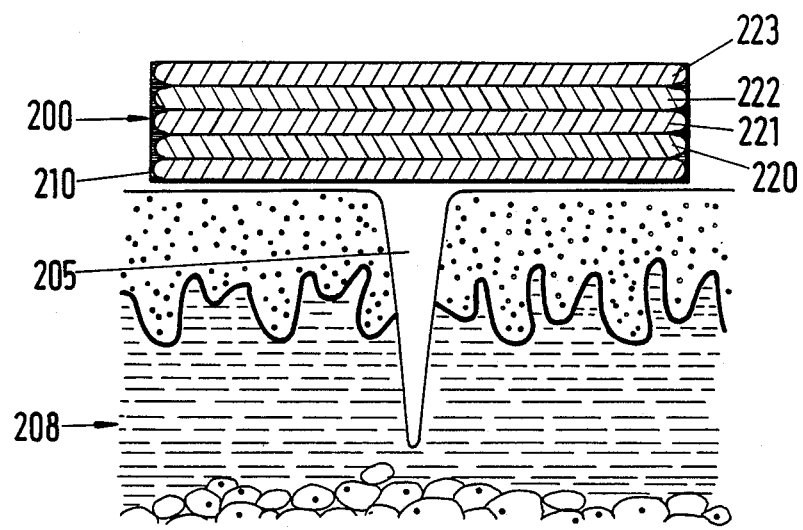
FIG. 3 Diagrammatically the use of a wound compress folded from the textile fabric being used on a skin part injured by a cut.

The use of a wound compress 200 formed by textile fabric 10 respectively open-width knitted web 100 on skin part 208 injured by a cut 205 is diagrammatically shown in FIG. 3. The hydrophobic covering layer 210 is located directly on the wound, whilst the hydrophilic, absorbent layers 220, 221, 222, 223 are arranged in the overlying fold layers.

As raw materials for the absorbent layer, staple fibre or filament yarns of cotton, viscose, linen or other absorbent materials are being used. The textile fabric is produced using known basic types of stitch linkage, such as e.g. fringe linkage, tricot linkage, etc. The dimensions of the yarns used are between 10 and 40 tex, preferably between 14 and 20 tex. Monofilaments and multifilaments, as well as staple fibre yarns are used for man-made fibres. The weft threads are formed from the corresponding materials. The man-made fibre yarns of synthetic polymers can be coated on the surface with silver or aluminum and it is also possible to use steamed-on layers of silver, aluminum or other suitable materials or compounds.

The textile fabric forming the wound compress is impregnated by antibacterial or medicinal agents. The impregnating agents can be constituted by quaternary ammonium compounds, e.g. N-cetyl pyridinium chloride, benzalkonium chloride, etc., as well as substances having disinfectant characteristics. It is also possible to apply Vaseline, i.e., petrolatum, to which medicaments, such as e.g. Peru balsam, sulphonamides, antibiotics, anasthetics, etc. have been added.

For marking the side facing the wound, it is possible to use dyes such as pigment dyes as well as suitable disperse or acid dyes and the like which can be added already to the raw material mass before transforming it.

What is claimed is:

1. A comprising a broad-width knitted or raschel-knitted web (100) of absorbent, hydrophilic cellulosic spun yarns (111, 112), a strip-like web section (120) of hydrophobic man-made fibers of synthetic polymers having a high surface tension interconnected to the knitted by looping within a plane, wherein the strip-like web section (120) is formed as central strip in the web (100) of knitted fabric (10), the knitted web and the strip-like web section being folded so as to form a wound pad (200) such that the web section (120) of the hydrophobic man-made fibers, as hydrophobic covering layer (210), forms the wound pad and layers of cellulosic spun yarns are located behind the web section to form absorbent layers (220, 221, 222, 223), wherein the diameters of the absorbent, hydrophilic cellulosic yarns and the hydrophobic man-made fibers range between 10 tex and 40 tex, wherein monofilaments, multifilament yarns and staple fiber yarns are used as the hydrophobic man-made yarns.

2. A wound dressing according to claim 1, wherein for marking the wound facing side, the man-made fibers of synthetic polymers are dyed with an indifferent, physiologically unobjectionable dye.

3. A wound dressing according to claim 1, wherein the wound dressing is impregnated with antibacterial or medicinal agents.

4. A wound dressing according to claim 1, wherein the man-made fibers of synthetic polymers are surface coated with silver or aluminum.

5. A wound dressing according to claim 1, wherein the cellulosic fiber yarns are cotton, viscose staple or cotton/viscose staple.

6. A wound dressing according to claim 1, wherein the man-made fibers are polyamide, polyester, polyethylene, polypropylene, polyacrylonitrile or polytetrafluoroethylene.

7. A wound dressing according to claim 1, wherein the diameters of the absorbent, hydrophilic cellulosic spun yarns and the man-made fibers used are between 14 and 20 tex.

8. A wound dressing according to claim 2, wherein the dye is selected from pigment dyes, disperse dyes or acid dyes.

9. A wound dressing according to claim 3, wherein the impregnating agent dressing quaternary ammonium compounds of N-cetyl pyridinium chloride or benzalkonium chloride.

10. A wound dressing according to claim 3, wherein the impregnating agent has disinfecting characteristics.

11. A wound dressing according to claim 3, wherein the impregnating agent is petrolatum mixed with Peru balsam, sulphonamides, antibiotics or anaesthetics.

* * * * *

UNITED STATES PATENT AND TRADEMARK OFFICE
CERTIFICATE OF CORRECTION

PATENT NO.   :   4,984,570

DATED        :   January 15, 1991

INVENTOR(S)  :   Günter Langen and Harald Jung

It is certified that error appears in the above-identified patent and that said Letters Patent is hereby corrected as shown below:

ON TITLE PAGE:

[75] Günter Langen, Wolfstein; Harald Jung, Kreimbach-Kaulbach, both of Fed. Rep. of Germany Signed and Sealed this Twenty-first Day of July, 1992

Attest:

DOUGLAS B. COMER

*Attesting Officer*     *Acting Commissioner of Patents and Trademarks*